United States Patent
Epperson

(10) Patent No.: US 6,248,094 B1
(45) Date of Patent: Jun. 19, 2001

(54) HYPODERMIC SYRINGE WITH RETRACTABLE NEEDLE

(76) Inventor: Frank E. Epperson, 1235 S. Birch St., Apartment No. 505, Aurora, CO (US) 80246

( * ) Notice: Subject to any disclaimer, the term of this patent is extended or adjusted under 35 U.S.C. 154(b) by 0 days.

(21) Appl. No.: 09/144,882

(22) Filed: Sep. 1, 1998

(51) Int. Cl.[7] .................................................... A61M 5/32
(52) U.S. Cl. .......................... 604/195; 604/200; 604/232; 604/110
(58) Field of Search ................................... 604/195, 107, 604/200, 201, 203, 206, 228, 232, 110

(56) References Cited

U.S. PATENT DOCUMENTS

| | | | |
|---|---|---|---|
| 3,890,971 | 6/1975 | Leeson et al. | 128/218 R |
| 4,675,005 | 6/1987 | DeLuccia | 604/110 |
| 4,781,684 | 11/1988 | Trenner | 604/110 |
| 5,098,390 * | 3/1992 | Wallingford | 604/195 |
| 5,116,319 * | 5/1992 | ven den Haak | 604/110 |
| 5,205,824 * | 4/1993 | Mazur | 604/110 |
| 5,575,774 * | 11/1996 | Chen | 604/110 |
| 5,785,687 * | 7/1998 | Saito | 604/110 |

\* cited by examiner

Primary Examiner—Sharon Kennedy
Assistant Examiner—Jeremy Thissell
(74) Attorney, Agent, or Firm—John E. Reilly

(57) ABSTRACT

A syringe having a retractable needle includes a carpule fitted within a hollow interior portion of a housing. The carpule includes first and second open ends and a needle-retaining member and a fluid-expelling member within the first and second ends to define a fluid chamber therebetween. The needle-retaining member is positioned adjacent a front end of the housing to allow one end of a needle to be inserted through the needle-retaining member and into the fluid chamber. A plunger pushes the fluid-expelling member forwardly to force substantially all the fluid within the fluid chamber through the needle. An attachment member fixed to the fluid-expelling member securely engages the needle-retaining member as the fluid chamber is emptied and the fluid-expelling member contacts the needle-retaining member. The plunger then retracts both the fluid-expelling member and the needle-retaining member along with the needle into the carpule to allow an operator to dispose of the carpule and the needle without touching the needle.

25 Claims, 3 Drawing Sheets

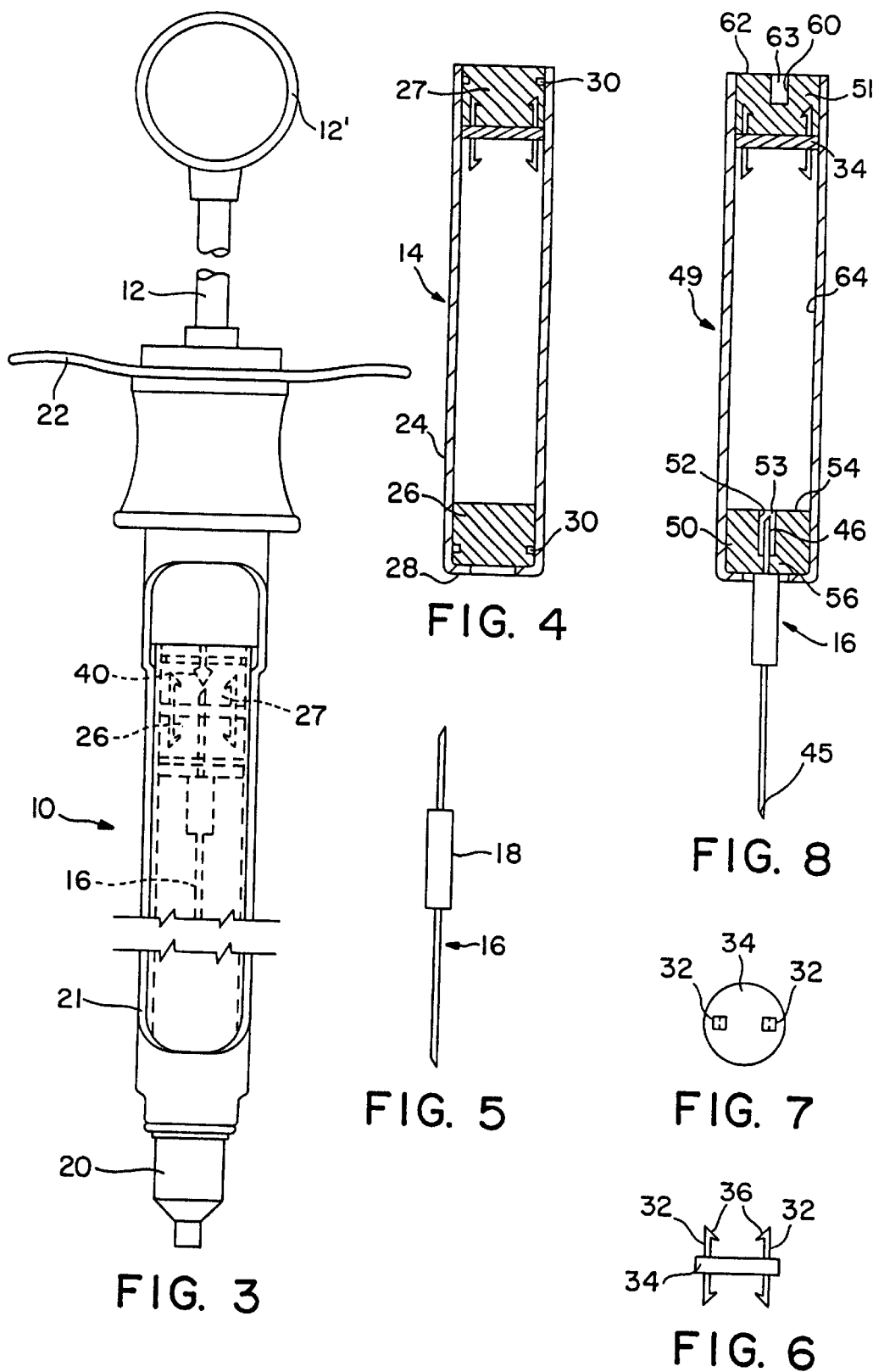

HYPODERMIC SYRINGE WITH RETRACTABLE NEEDLE

CROSS-REFERENCE TO CO-PENDING PROVISIONAL APPLICATION

This is a continuation-in-part application of U.S. Provisional Patent Application Ser. No. 60/073,748, filed Feb. 5, 1998. Priority benefits are claimed pursuant to 35 U.S.C. § 119(e) and 37 C.F.R. § 1.78.

BACKGROUND AND FIELD OF THE INVENTION

This invention relates to hypodermic syringes and more particularly relates to a novel and improved syringe having a retractable needle assembly to prevent cross-contamination or other accidental injury when delivering an injectable solution to a patient.

Various types of syringes have been devised with a retractable needle assembly, for example, to prevent reuse or improve the safety features of the syringe. Representative devices are those illustrated and disclosed in U.S. Pat. No. 3,890,971 to T. A. Leeson et al, U.S. Pat. No. 4,675,005 to J. DeLuccia and U.S. Pat. No. 4,781,684 to L. E. Trenner. However, each of these references describe a single-use, disposable syringe having a unique fluid containment system which complements the respective retractable needle assembly. Thus, it is highly desirable to provide a retractable needle assembly for use in non-disposable syringes of the type which employ pre-filled, disposable carpules for containing the medical solution.

SUMMARY OF THE INVENTION

It is therefore an object of the present invention to provide for a novel and improved type of syringe which employs a retractable needle in combination with carpules for containing the injectable solution.

It is another object of the present invention to provide for a novel and improved syringe which prevents accidental injury to those operating the syringe by retracting the used needle within the expendable carpule following the injection.

It is a further object of the present invention to provide for a novel and improved method of operating a retractable needle syringe in a manner which prevents injury to an operator.

It is another object of the present invention to provide the functionality of the retractable needle with syringes and carpules that are familiar to the operator.

It is a further object of the present invention to utilize a retractable needle assembly with a standard dental syringe, although other applications will become readily apparent.

In accordance with the present invention, an improved syringe has been devised in which a carpule is fitted within a hollow interior portion of a cylindrical housing. The carpule preferably includes first and second open ends and a needle-retaining member and a fluid-expelling member disposed within the respective open ends to define a fluid chamber therebetween. The carpule is fitted within the cylindrical housing so that the needle-retaining member is positioned adjacent a front end of the housing, thereby allowing one end of a needle to be inserted through the needle-retaining member and into the fluid chamber of the carpule while the opposite end of the needle projects from the front end of the housing for injecting a patient. A plunger is connected to the fluid-expelling member through a rear end of the housing to push the fluid-expelling member forward and force substantially all the fluid within the fluid chamber through the needle. The plunger includes a penetrating end which securely engages the fluid-expelling member and allows the fluid-expelling member to be retracted toward the rear end of the syringe.

In a preferred embodiment, an attachment means is fixed to a front surface of the fluid-expelling member to securely engage a rear surface of the needle-retaining member as the last of the fluid is expelled from the fluid chamber and the fluid-expelling member contacts the needle-retaining member. The plunger is then retracted to pull the needle-retaining member along with the fluid-expelling member toward the second end of the carpule. The needle remains frictionally engaged by the needle-retaining member and is thus retracted within the carpule together with the fluid-expelling member and the needle-retaining member. The carpule may then be removed from the syringe housing and disposed of together with the used needle without requiring the operator to handle or even touch the needle.

In another embodiment, the needle-retaining member includes a receptacle defined in the rear surface to receive the end of the needle inserted through the needle-retaining member. The end of the needle does not extend beyond the rear surface of the needle-retaining member, and the receptacle is in fluid communication with the fluid chamber of the carpule so that any fluid within the fluid chamber must flow into the receptacle before passing through the needle. The receptacle thus serves to enhance the contact between the fluid-expelling member and the needle-retaining member while also ensuring that substantially all of the fluid within the fluid chamber drains into the receptacle where it is then expelled through the needle.

The above and other objects of the present invention will become more readily appreciated and understood from a consideration of the following detailed description of preferred and modified forms of the present invention when taken together with the accompanying drawings in which:

BRIEF DESCRIPTION OF THE DRAWINGS

FIG. 3 is another front view in elevation of the preferred form of syringe with the needle shown in a retracted position;

FIG. 4 is a view in section of the carpule of the preferred form of syringe;

FIG. 5 is a front elevational view of the needle employed with the syringe;

FIG. 6 is a front view in elevation of a barb portion of the carpule;

FIG. 7 is a plan view of the barb portion shown in FIG. 6;

FIG. 8 is a view in section of a first alternative embodiment of the carpule;

DETAILED DESCRIPTION OF PREFERRED EMBODIMENT

Figure 1:
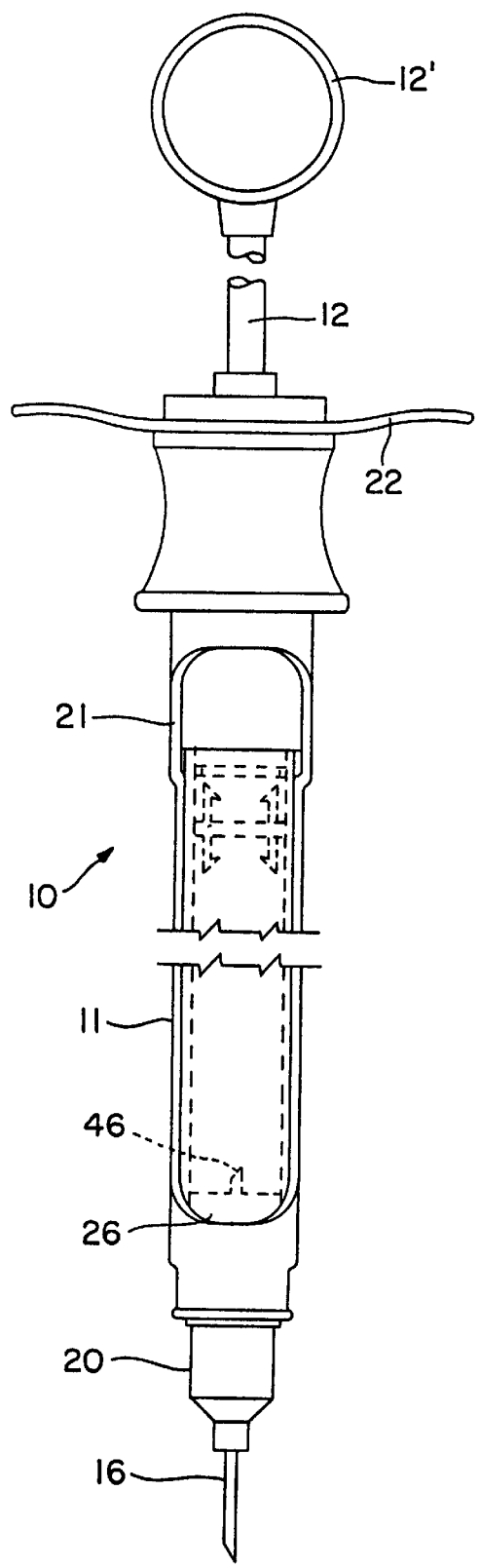
FIG. 1 is a front elevational view of a preferred form of syringe.

Referring in more detail to the drawings, there is shown in FIGS. 1–4 a preferred form of hypodermic syringe 10 which is broadly comprised of a syringe housing 11 having a plunger 12, a carpule 14 slidable within the syringe 10 and containing a solution to be injected, and a needle assembly made up of a needle 16 and surrounding collar 18 for insertion through a hub 20 at the leading end of the syringe 10.

For the purpose of illustration but not limitation, the syringe 10 is essentially in the form of a standard dental syringe used to administer anaesthetics. The housing 11 of the syringe 10 is in the form of an elongated hollow cylinder having recessed portions 21 and 21' and a rim or ledge 22 which defines a finger grip at its rear end opposite to the hub 20. The hub 20 is slightly reduced in diameter and internally threaded for engagement with a fitting 23 which couples the hub 20 to the lower end of the housing 11. An important feature of the invention resides in the construction and arrangement of the carpule 14, as shown in detail in FIG. 4. The carpule is made up of an elongated tube 24 of clear plastic or glass which is closed at opposite ends by circular plugs 26 and 27. The tube 24 is of uniform diameter conforming closely to the inner diameter of the housing 11 except for an inturned edge 28 at its leading end to retain the plug 26 against release from the end of the tube 24. Each of the plugs 26, 27, the plug 26 defining a needle-retaining member for the needle 16 and the plug 27 defining a fluid-expelling member as hereinafter described is composed of a rubber or rubber-like material and each is provided with an external circumferential groove 30. A fluid or injectable solution as described is retained in sealed relation in the tube 24 by the plugs 26, 27. A plurality of sharp, rigid barbs 32, preferably made from stainless steel, are mounted in spaced circumferential relation to one another in a disk 34 which is positioned against the front face of the rear plug 27 so that rearward ends of the barbs penetrate into the thickness of the plug 27 and, by virtue of their pointed but hooked ends 36, the barbs 32 are anchored securely in position in the plug 27.

Figure 2:
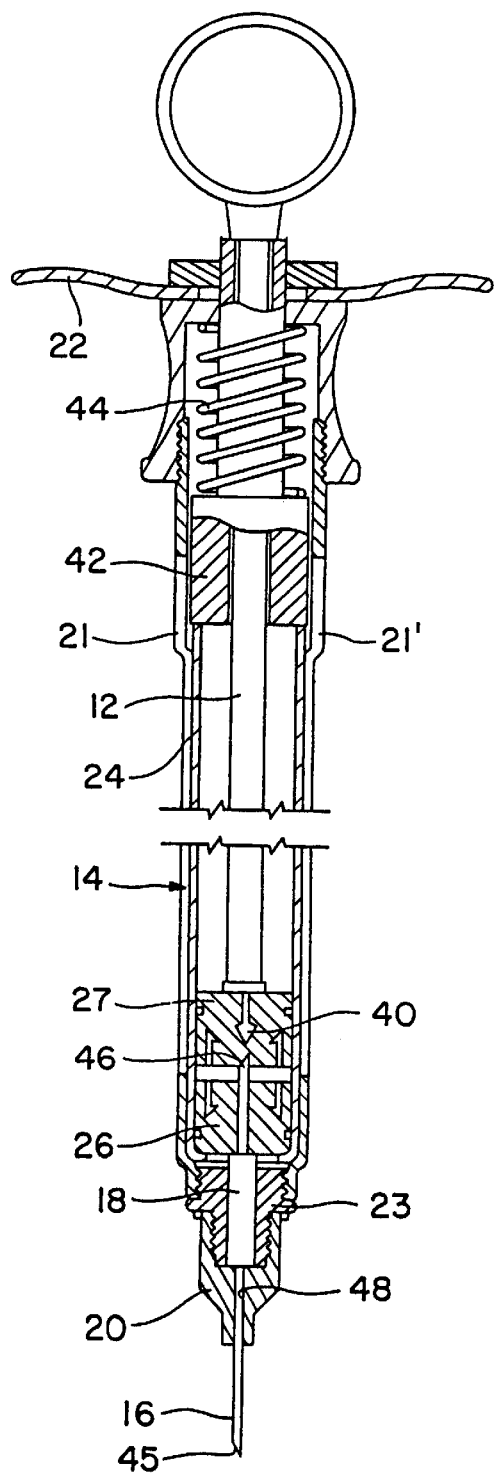
FIG. 2 is a longitudinal sectional view of the syringe assembly shown in FIG. 1.

The plunger 12 extends through a central opening in the rearward end of the syringe and includes a spear point 40 at its leading end which is aligned with the longitudinal axis of the carpule and will penetrate the rearward end of the plug 27 when advanced through the barrel 11, as shown in FIG. 2. A sleeve 42 assists in maintaining the plunger in centered relation to the plug 27 and is backed by a suitable return spring 44.

As noted earlier, the needle 16 and collar 18 are mounted in the hub 20, the needle 16 being formed in a well-known manner with sharpened ends 45 and 46, the leading end 45 normally extending through a central bore 48 in the hub 20 and the trailing end 46 extending rearwardly through the plug 26 as shown in FIG. 1. When the ring-like gripping end 12' of the plunger 12 is grasped and the plunger 12 advanced forwardly, it will force the plug 27 forwardly to expel the contents of the carpule 14 through the needle 16. As shown in FIG. 2, when the plug 27 approaches its forward end limit of movement the leading ends of the barbs 32 will penetrate the body of the plug 26. Similarly, the pointed end 46 of the needle 16 penetrates through the disk 34 and a limited distance into the plug 27 depending upon the relative length of the needle 16 extending rearwardly from the collar 18. Most significantly, however, the barbed leading ends 36 of the barbs 32, with the assistance of any vacuum created between the plugs 26, 27, will resist any tendency of the plug 27 to be separated from the plug 26 when the plunger 12 is retracted rearwardly through the housing 11, as shown in FIG. 3. On the other hand, air is free to pass between the walls of the carpule 14 and syringe 10 into the space in front of the plug 26 so as to avoid creation of a vacuum between the needle assembly and plug 26; and similarly, there is sufficient clearance between the leading end of the needle 16 and bore 48 of the hub 20 as well as between the collar 18 and fitting 23 so that the needle will freely slide rearwardly with the movement of the plugs 26 and 27. Accordingly, the plug 26 as well as the needle 16 will follow the plug 27 as it is withdrawn rearwardly by retraction of the plunger 12 until the leading end of the needle is fully within the interior of the housing 11.

As seen from FIG. 6, a pair of barbs 32 are anchored in the disk 34 but additional barbs may be employed if desired. Also, in usual applications, the frictional engagement between the trailing end of the needle 16 and plug 26 as well as the vacuum between the plugs 26 and 27 is sufficient to assure that the needle 16 will follow the rearward movement of the plunger 12 until the needle 16 is fully within the barrel.

In assembly, the carpule 14 is inserted into the syringe 10, and the fitting 23 is threaded onto the end of the syringe 10 until the needle 16 penetrates through the front plug 26 into the fluid within the carpule, the collar 18 on the needle 16 being confined between the hub 20 and the plug 26 to prevent movement in either direction.

From the foregoing, the leading end of the needle 16 is inserted into the patient, following which the plunger 12 is depressed to advance forwardly through the housing 11 thereby forcing the rear plug 27 to expel the fluid through the needle 16 into the patient. When the carpule 14 is evacuated the barbs 32 on the rear plug 27 are forced into the front plug 26 and the spear point 40 on the plunger 12 is forced into the rear plug 27. The plunger 12 is then retracted to withdraw the plugs 26, 27 and the needle 16. Any accidental injury to the operator is avoidable because the needle 16 will remain fully enclosed in the carpule 14.

An alternative embodiment of the carpule 49 is shown in FIG. 8 with alterations to the front and rear plugs 50 and 51, respectively. A central counterbore 52 formed within the front plug 50 provides a receptacle 53 which receives the trailing end 46 of the needle 16. The receptacle 53 provides a lowermost drain point which allows substantially all of the fluid within the carpule 49 to be expelled through the needle 16. Simultaneously, the receptacle 53 surrounds the trailing end 46 of the needle 16 to prevent the trailing end 46 from extending beyond a rear face 54 of the front plug 50, thereby allowing flush contact between the front plug 50 and the disk 34 attached to the rear plug 51. Thus, the inclusion of the counterbore 52 ensures that substantially all of the fluid within the carpule 49 is dispensed to the patient while enhancing the contact between the front and rear plugs 50 and 51, respectively.

While the counterbore 52 reduces the thickness of the portion 56 of the front plug 50 through which the trailing end 46 of the needle 16 penetrates, the portion 56 remains sufficiently thick to securely attach the needle 16 to the front plug 50. Therefore, the inclusion of the counterbore 52 does not significantly impact the ability of the rear plug 51 to engage the front plug 50 and retract both the front plug 50 and the needle 16 within the carpule 49.

The alternative embodiment of the rear plug 51 also includes a counterbore 60 formed within a rear face 62 thereof, as shown in FIG. 8. The counterbore 60 is preferably formed to a lesser depth than that of the counterbore 52 formed within front plug 50. The counterbore 60 essentially provides a recessed portion 63 which acts to relieve the stress applied to the plug 51 when the spear point 40 of the plunger 12 is inserted into the rear plug 51. In the absence of the counterbore 60, the plug 51 tends to expand with insertion of the spear point 40 therein. Expansion of the plug 51 increases the frictional drag between the plug 51 and an interior surface 64 of the carpule 49 which, in turn, increases the force required to push or retract the rear plug 51, particularly when the plug 51 is attached to the front plug 50 by the barbed disk 34. Thus, the recessed portion 63 provides a starting point for insertion of the spear point 40 of the plunger 12.

Figure 9:
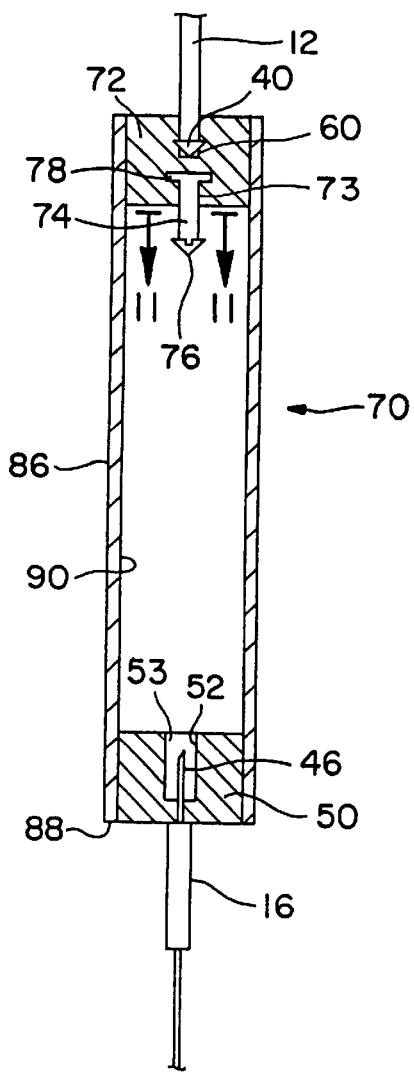
FIGS. 9 and 10 are sectional views of a second alternative embodiment of the carpule.
Figure 10:
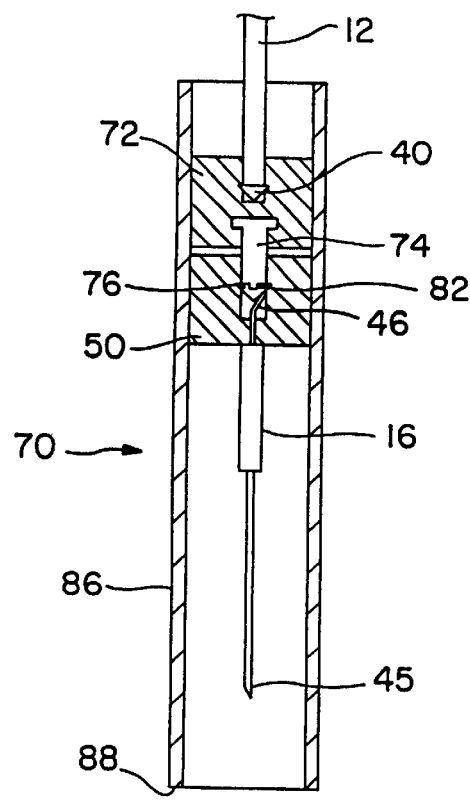
Figure 11:
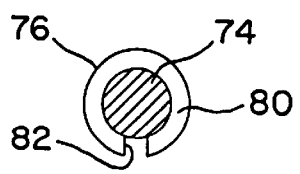
FIG. 11 is an enlarged cross-sectional view of the spear point in the embodiment shown in FIGS. 9 and 10 taken about a line passing through the shaft of the barb directly behind the spear point.

A second alternative embodiment of the carpule 70 is shown in FIGS. 9 to 11 with further alterations to the rear plug 72. The rear plug 72 includes a counterbore 60 for receiving the spear point 40 of the plunger 12, substantially as described with respect to the first alternative embodiment of the rear plug 50 (FIG. 8). However, the carpule 70 does not include the disk 34 with the opposite facing barbs 32 as described with respect to the first embodiment of the carpule 14 in FIGS. 1–7. Rather, the rear plug 72 includes a single barb 73 comprising a cylindrical shaft 74, preferably made from a plastic material, which terminates in a spear point 76 similar in shape and function to the spear point 40 of the plunger 12. An enlarged base 78 at an opposite end of the shaft 74 is preferably inserted within the rear plug 72 below the level of the counterbore 60 so that the spear point 76 is centered within the carpule 70 and aligned with the counterbore 52 in the front plug 50, as shown in FIGS. 9 and 10.

An upper shoulder portion 80 of the spear point 76 includes a recessed portion 82 as shown in FIG. 11. This recessed portion 82 allows fluid to be forced out of the receptacle 53 of the front plug 50 and past the shaft 74 as the spear point 76 advances through the counterbore 52. As the barb 73 extends further within the receptacle 53, the spear point 76 preferably contacts and wedges against the trailing end 46 of the needle 16, as shown in FIG. 10. Wedging the needle 16 in this fashion further ensures that the needle 16 will remain securely engaged to the front plug 52. Once the spear point 76 has penetrated a sufficient distance within the receptacle 53 so that the shoulder portion 80 of the spear pont 76 is securely embedded within the counterbore 52, the plunger 12 is withdrawn to retract the needle 16 inside the carpule 70, as shown in FIG. 10.

The use of the alternative carpule 70 in place of the carpule 14 is driven primarily by the lower cost of the plastic barb 73 in place of the relatively expensive stainless steel barbs 32 utilized within the carpule 14. Additionally, the alternative carpule 70 is comprised of an alternative elongated tube 86 which is similar in shape to the cylinder 24 of the carpule 14 but which includes a straight leading edge 88 as shown in FIGS. 9 and 10. Thus, the alternative elongated tube 86 does not include an inturned edge at its leading end, similar to the edge 28 of the tube 24 shown in FIG. 4, to retain the front plug 50, but relies on the frictional force between the front plug 50 and an interior surface 90 of the tube 86. The omission of such an inturned edge further reduces the cost of the alternative carpule 70 relative to the carpule 14.

Although the invention has been described primarily in connection with a standard type of dental syringe as described, it will be appreciated that it has useful applications for other types of medical syringes and for virtually any gauge of needle.

It is therefore to be understood that while preferred and modified forms of the present invention are herein set forth and disclosed, other modifications and changes may be made therein without departing from the spirit and scope of the present invention as defined by the appended claims.

I claim:

1. A syringe comprising:

an elongated housing having a front end for attachment of a needle and a rear end for insertion of a plunger, said housing defining a substantially hollow interior portion between said front and rear ends;

a carpule disposed in said housing comprising a tube having first and second open ends, said carpule including a needle-retaining member slidably disposed within said first open end and a fluid-expelling member disposed within said second open end, said needle-retaining member and said fluid-expelling member each forming a fluid-tight seal with an interior surface of said tube to define a fluid chamber between said members, and said carpule disposed within said substantially hollow interior portion of said housing to position said needle-retaining member adjacent said front end of said housing;

a needle having a leading end normally projecting from said front end of said housing for injecting a patient and a trailing end extending into said front end of said housing and through said needle-retaining member to draw fluid from said fluid chamber;

a plunger having a gripping end and an opposing penetrating end, said penetrating end securely engaging said fluid-expelling member to push said fluid-expelling member toward said first end of said carpule and expel substantially all said fluid within said fluid chamber through said needle; and attachment means connected to said fluid-expelling member within said fluid chamber, said attachment means securely engaging said needle-retaining member as said plunger pushes said fluid-expelling member to said first end of said carpule whereby retraction of said plunger toward said second open end of said carpule causes retraction of said needle-retaining member away from said open end and retraction of said needle into said carpule.

2. A syringe according to claim 1, wherein said trailing end of said needle is frictionally engaged by said needle-retaining member so as to move together with said needle-retaining member toward said second open end of said carpule.

3. A syringe according to claim 1, wherein said carpule has a length sufficient to accommodate said leading end of said needle within said first open end of said carpule as said needle-retaining member and said trailing end of said needle are retracted within said second open end of said carpule.

4. A syringe according to claim 1, wherein a gap between an exterior surface of said tube and an interior surface of said elongated housing allows air to fill said first open end of said carpule as said needle-retaining member is withdrawn toward said second open end of said carpule to prevent formation of a vacuum between said needle-retaining member and said front end of said housing.

5. A syringe according to claim 4, further comprising:

a sleeve for supporting said plunger as said plunger moves within said housing, said sleeve slidably positioned adjacent said rear end of said housing to allow for loading of said carpule within said hollow interior portion of said housing; and a return spring biasing said sleeve into contact with said second open end of said carpule once said carpule is loaded within said hollow interior portion of said housing.

6. A syringe according to claim 1, wherein:
said needle-retaining member comprises a first plug; and
said fluid-expelling member comprises a second plug.

7. A syringe according to claim 6, wherein said attachment means comprises:
at least one barb having first and second opposing ends, said second end secured to said second plug and said first end adapted to securely engage said first plug as said second plug is pushed into contact with said first plug.

8. A syringe according to claim 7, wherein:
said attachment means further comprises at least two barbs arranged opposite to one another; and
said first and second barb ends are shaped in the form of hooks.

9. A syringe according to claim 8, wherein:
said attachment means further comprises a circular disk having a circumference substantially equal to a circumference of said first and second plugs; and
said at least two barbs are mounted on said disk with said first and second hooked ends positioned on opposite sides of said disk.

10. A syringe according to claim 7, wherein:
said first end of said at least one barb includes a pointed end; and
a rear surface of said first plug includes a counterbore to define a recessed portion for receiving said pointed end.

11. A syringe according to claim 6, wherein said first open end of said carpule includes an inturned edge to retain said first plug against release from said first open end.

12. A syringe according to claim 6, wherein said first and second plugs are formed from a rubber material.

13. A syringe according to claim 2, wherein said needle includes a collar positioned between said leading and trailing ends, said collar engaging a front face of said needle-retaining member to prevent movement of said needle relative to said needle-retaining member toward said second open end of said carpule.

14. A syringe according to claim 13, further comprising:
a hub attached to said front end of said elongated housing, said hub contacting said needle collar opposite said needle-retaining member to prevent withdrawal of said trailing end of said needle from said needle-retaining member, and said hub defining a central bore through which said leading end of said needle extends.

15. A syringe according to claim 2, wherein a rear surface of said needle-retaining member includes a counterbore to define a receptacle for receiving said trailing end of said needle, said receptacle facing said second open end of said carpule, and wherein said fluid within said fluid chamber flows into said receptacle prior to being expelled through said needle.

16. A syringe according to claim 1, wherein a rear surface of said fluid-expelling member includes a counterbore to define a recessed portion for receiving said penetrating end of said plunger.

17. A syringe comprising:
an elongated housing having a front end for attachment of a needle and a rear end for insertion of a plunger, said housing defining a substantially hollow interior portion between said front and rear ends;
a carpule comprising a tube having first and second open ends, said carpule including a needle-retaining member slidably disposed within said first open end and a fluid-expelling member slidably disposed within said second open end, said needle-retaining member and said fluid-expelling member each forming a fluid-tight seal with an interior surface of said tube to define a fluid chamber between said members, said needle-retaining member having a counterbore in a rear surface to define a receptacle in fluid communication with said fluid chamber, and said carpule disposed within said substantially hollow interior portion of said housing to position said needle-retaining member adjacent said front end of said housing;
a needle having a leading end normally projecting from said front end of said housing for injecting a patient and a trailing end extending through said needle-retaining member and into said receptacle;
a plunger having a gripping end and an opposing penetrating end, said penetrating end positively engaging said fluid-expelling member to push said fluid-expelling member toward said first end of said carpule and expel substantially all said fluid within said fluid chamber into said receptacle and through said needle; and
attachment means including a piercing end connected to said fluid-expelling member within said fluid chamber, said attachment means penetrating said needle-retaining member as said plunger pushes said fluid-expelling member to said first end of said carpule whereby retraction of said plunger toward said second open end of said carpule causes withdrawal of said needle into said carpule.

18. A syringe according to claim 17, wherein a rear surface of said fluid-expelling member includes a counterbore to define a recessed portion for receiving said piercing end of said plunger.

19. A syringe according to claim 17, wherein:
said piercing end in the form of at least one barb extending forwardly from said fluid-expelling member; and
said needle-retaining member receives said barb(s) within said receptacle when said plunger pushes said fluid-expelling member to said first end of said carpule.

20. A syringe according to claim 19, wherein said piercing end has a spear point including a recessed portion to expel fluid from said receptacle.

21. A syringe according to claim 20, wherein said spear point is operative to wedge said trailing end of said needle within said receptacle.

22. A carpule for use with a retractable needle syringe, said carpule comprising:
a tube having first and second open ends;
a needle-retaining member slidably disposed within said first open end and forming a fluid-tight seal with an interior surface of said tube;
a fluid-expelling member disposed within said second open end and forming a fluid-tight seal with said interior surface of said tube, said needle-retaining member and said fluid-expelling member defining a fluid chamber between said members, and said needle-retaining member frictionally engaging one end of a needle for expelling fluid from said fluid chamber; and
attachment means including a piercing end connected to said fluid-expelling member for positively engaging said needle-retaining member as fluid is expelled from said fluid chamber whereby retraction of said plunger causes retraction of said needle-retaining member and needle into said carpule.

23. A method of operating a retractable needle syringe, comprising the steps of:

providing an elongated housing having a front end, a rear end and a substantially hollow interior portion between said front and rear ends;

loading a carpule within said substantially hollow interior portion of said housing, said carpule comprising a tube having first and second open ends, said carpule including a needle-retaining member slidably disposed within said first open end and a fluid-expelling member slidably disposed within said second open end, said needle-retaining member and said fluid-expelling member each forming a fluid-tight seal with an interior surface of said tube to define a fluid chamber between said members, and wherein said loading step includes positioning said needle-retaining member adjacent said front end of said housing;

inserting a trailing end of a needle through said needle-retaining member and into said fluid chamber, said needle including a leading end normally projecting from said front end of said housing for injecting a patient;

inserting a penetrating end of a plunger into said rear end of said housing to securely engage said penetrating end to said fluid-expelling member;

pushing a gripping end of said plunger toward said rear end of said housing to push said fluid-expelling member toward said first end of said carpule and expel substantially all said fluid within said fluid chamber through said needle;

forcing attachment means having a piercing end connected to said fluid-expelling member into secure engagement with said needle-retaining member at said first end of said carpule; and retracting said gripping end of said plunger to withdraw said needle-retaining member and needle into said carpule.

24. A method according to claim 23, wherein said step of retracting said gripping end of said plunger further includes withdrawing said needle completely within said carpule, said method further comprising said step of:

removing said carpule from said substantially hollow interior portion of said housing while said needle remains within said carpule.

25. A method according to claim 23, further comprising said steps of:

attaching a hub to said front end of said elongated housing to prevent withdrawal of said trailing end of said needle from said needle-retaining member; and extending said leading end of said needle through a central bore defined in said hub.

\* \* \* \* \*